United States Patent
Ohashi et al.

(10) Patent No.: US 10,086,672 B2
(45) Date of Patent: Oct. 2, 2018

(54) AIR SOURCE DEVICE

(71) Applicant: TOYOTA JIDOSHA KABUSHIKI KAISHA, Toyota-shi, Aichi-ken (JP)

(72) Inventors: Hideki Ohashi, Chiryu (JP); Ryo Kanda, Nissin (JP); Jun Tokumitsu, Toyota (JP); Shogo Tanaka, Toyota (JP); Kohtaroh Okimura, Nissin (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 172 days.

(21) Appl. No.: 15/361,200

(22) Filed: Nov. 25, 2016

(65) Prior Publication Data
US 2017/0158018 A1 Jun. 8, 2017

(30) Foreign Application Priority Data
Dec. 4, 2015 (JP) ................. 2015-237280

(51) Int. Cl.
| | |
|---|---|
| B60G 17/00 | (2006.01) |
| B60G 17/015 | (2006.01) |
| F04B 41/02 | (2006.01) |
| F04B 49/08 | (2006.01) |
| F04B 53/10 | (2006.01) |
| B60G 17/052 | (2006.01) |
| F04B 49/06 | (2006.01) |
| G01N 7/00 | (2006.01) |

(52) U.S. Cl.
CPC ..... *B60G 17/0523* (2013.01); *B60G 17/0528* (2013.01); *F04B 41/02* (2013.01); *F04B 49/06* (2013.01); *F04B 49/065* (2013.01); *F04B 53/10* (2013.01); *G01N 7/00* (2013.01); *B60G 2202/152* (2013.01); *B60G 2400/51222* (2013.01); *B60G 2400/952* (2013.01); *B60G 2500/02* (2013.01); *B60G 2500/205* (2013.01); *B60G 2500/30* (2013.01); *F04B 2205/063* (2013.01)

(58) Field of Classification Search
CPC .... B60G 17/00; B60G 17/015; B60G 17/052; B60G 17/0523; B60G 17/0528; B60G 2202/152; B60G 2400/952; B60G 2500/02; B60G 2500/30; B60G 2500/205; F04B 41/02; F04B 49/06; F04B 49/065; F04B 49/08; F04B 53/10; F04B 2205/06; G01N 7/00
See application file for complete search history.

(56) References Cited

U.S. PATENT DOCUMENTS

| | | | |
|---|---|---|---|
| 7,624,994 B2 * | 12/2009 | Stegmann ............ | B60G 17/052 280/124.161 |
| 2015/0151603 A1* | 6/2015 | Kondo ................ | B60G 17/017 280/6.157 |

FOREIGN PATENT DOCUMENTS

| | | | | |
|---|---|---|---|---|
| JP | H03-70615 A | | 3/1991 | |
| JP | 2017100642 A | * | 6/2017 | ......... B60G 17/0523 |

\* cited by examiner

*Primary Examiner* — Nguyen Ha
(74) *Attorney, Agent, or Firm* — Oliff PLC

(57) ABSTRACT

An air source device includes: a tank; a compressor; an intake valve; and an ECU configured to acquire an intake amount, which is an amount of air sucked from an outside and supplied to the tank by the compressor, based on an increasing amount of a tank pressure, which is a pressure of the air accommodated in the tank, the increasing amount being an increasing amount from a time point when the intake valve is estimated to be changed from a closed state to an opened state.

6 Claims, 8 Drawing Sheets

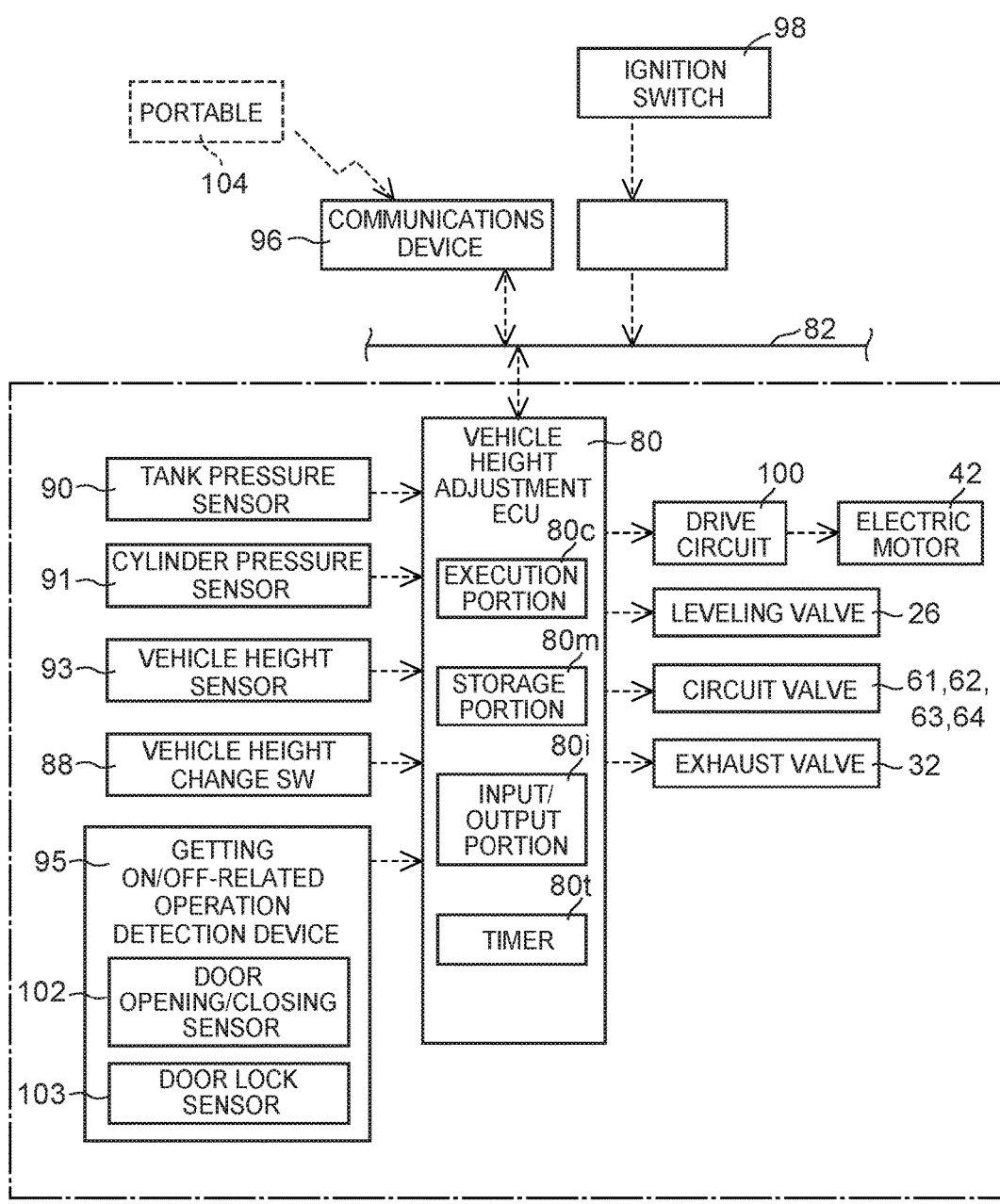

AIR SOURCE DEVICE

INCORPORATION BY REFERENCE

The disclosure of Japanese Patent Application No. 2015-237280 filed on Dec. 4, 2015 including the specification, drawings and abstract is incorporated herein by reference in its entirety.

BACKGROUND

1. Technical Field

The disclosure relates to an air source device including a tank in which air is accommodated.

2. Description of Related Art

In an air source device described in Japanese Patent Application Publication No. 3-70615 (JP 3-70615 A), a pressure of air accommodated in a tank is kept within a set range by control of a compressor. When a tank pressure, which is a pressure of the air accommodated in the tank decreases to be lower than a lower limit of the set range, the compressor is started, and when the tank pressure reaches an upper limit, the compressor is stopped.

SUMMARY

The disclosure provides an air source device that can accurately acquire an intake amount of air sucked from an outside of a device and supplied to a tank.

An air source device according to an aspect of the disclosure includes: a tank in which air is accommodated; a compressor; an intake valve provided between a suction-side portion, which is a part on a suction side of the compressor, and an outside of the air source device, the intake valve being configured such that, when a pressure of the air in the suction-side portion is not less than an atmospheric pressure, which is a pressure of the outside, the intake valve is in a closed state, but when the pressure of the air in the suction-side portion becomes lower than the atmospheric pressure, the intake valve is changed to an opened state; and an ECU configured such that the ECU controls an amount of the air sucked from the outside and supplied to the tank by an operation of the compressor, the ECU estimates whether or not the intake valve is changed from the closed state to the opened state, based on a pressure of the air in the air source device, and the ECU acquires an intake amount, which is an amount of the air sucked from the outside and supplied to the tank by the compressor, based on an increasing amount of a tank pressure, which is a pressure of the air accommodated in the tank, the increasing amount being an increasing amount from a time point when the intake valve is estimated to be changed from the closed state to the opened state. In the above aspect, the intake valve is provided on the suction side of the compressor, and the air is sucked from the outside of the air source device via the intake valve and supplied to the tank. Here, the amount of the air sucked from the outside of the air source device and supplied to the tank is acquired based on a change amount of the tank pressure from a time point when the intake valve is changed from the closed state to the opened state. The intake valve is not a solenoid valve, but a mechanical valve that is opened/closed due to a difference in pressure between the suction-side part of the compressor and the outside of the air source device. A time point when the intake valve is changed from the closed state to the opened state is estimated based on the pressure of the air source device, and an intake amount is acquired based on the change amount of the tank pressure from the estimated time point. Hereby, it is possible to accurately acquire the intake amount, which is the amount of the air sucked from the outside of the air source device and supplied to the tank.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein:

FIG. 2 is a conception diagram illustrating peripheral parts of a vehicle height adjustment ECU of the vehicle height adjustment system;

DETAILED DESCRIPTION OF EMBODIMENTS

The following describes a vehicle height adjustment system including an air source device according to one embodiment of the disclosure in detail with reference to the drawings.

Figure 1:
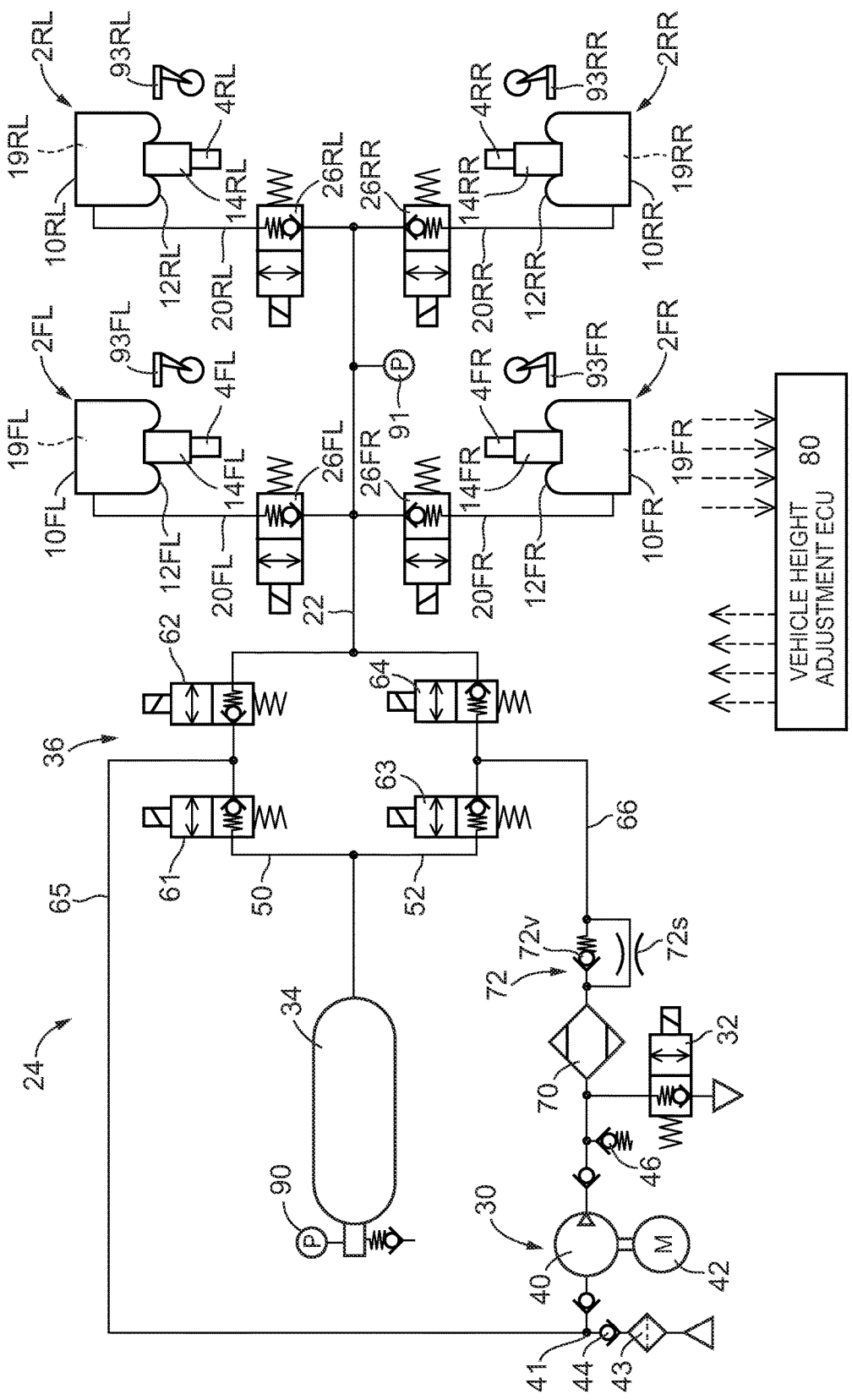
FIG. 1 is a circuit diagram illustrating a vehicle height adjustment system including an air source device according to Embodiment 1 of the disclosure.

In the vehicle height adjustment system according to the present embodiment, as illustrated in FIG. 1, air cylinders 2FL, 2FR, 2RL, 2RR as vehicle height adjustment actuators and shock absorbers 4FL, 4FR, 4RL, 4RR are provided in parallel to each other between a wheel-assembly-side member and a vehicle-body-side member (not shown) so as to correspond to respective wheel assemblies provided in a vehicle on right/left and front/rear sides. The shock absorber 4FL, 4FR, 4RL, 4RR includes a cylinder body provided in the wheel-assembly-side member, and a piston provided in the vehicle-body-side member. Hereinafter, in the present specification, in a case where it is necessary to distinguish the air cylinders 2 and the like according to positions of the wheel assemblies, reference signs FL, FR, RL, RR indicative of respective positions of the wheel assemblies are assigned so as to distinguish them from each other. However, in a case where it is not necessary to distinguish them according to the positions of the wheel assemblies and in a case where they are generally referred to, the reference signs FL, FR, RL, RR and the like indicative of respective positions of the wheel assemblies are omitted. The air cylinder 2 includes a chamber 10 as a cylinder body provided in the vehicle-body-side member, a diaphragm 12 fixed to the chamber 10, and an air piston 14 provided so as to be immovable in an up-down direction relative to the diaphragm 12 and a cylinder body of the shock absorber 4. Inner parts of them serve as an air chamber 19 as a pressure-medium chamber. When the air piston 14 is moved in the up-down direction relative to the chamber 10 by supplying and discharging of air in the air chamber 19, the cylinder body and the piston of the shock absorber 4 are hereby relatively moved in the up-down direction. This accordingly changes a vehicle height, which is a distance between the wheel-assembly-side member and the vehicle-body-side member.

An air supply/discharge device 24 as a pressure-medium supply/discharge device is connected to the air chamber 19 of the air cylinder 2 via an individual passage 20 and a common passage 22. The individual passage 20 is provided with a leveling valve 26. The leveling valve 26 is a normally closed solenoid valve. In an opened state, the leveling valve 26 permits bidirectional flows of the air, and in a closed state, the leveling valve 26 prevents a flow of the air from the air chamber 19 to the common passage 22, but when a pressure of the common passage 22 becomes higher than a pressure of the air chamber 19 by a setting pressure or more, the leveling valve 26 permits a flow of the air from the common passage 22 to the air chamber 19.

The air supply/discharge device 24 includes a compressor device 30, an exhaust valve 32, a tank 34, a switch device 36, and so on. The compressor device 30 includes a compressor 40, an electric motor 42 for driving the compressor 40, an intake valve 44, which is a check valve provided between a connecting portion 41 on an intake side of the compressor 40 and an outside (atmospheric air) of the vehicle height adjustment system, a relief valve 46 provided on a discharge side of the compressor 40, and so on. When a pressure of the air in the connecting portion 41 on the intake side of the compressor 40 becomes lower than an atmospheric pressure, the air is sucked by the compressor 40 from the outside of the vehicle height adjustment system via a filter 43 and the intake valve 44. Further, when a discharge pressure of the compressor 40 becomes high, the air is discharged to the outside of the vehicle height adjustment system via the relief valve 46. The tank 34 is configured to store the air in a pressurized state, such that the air is stored in a state where its pressure is higher than a predetermined initial pressure. Further, when an amount of the air supplied to the tank 34 increases, the tank pressure, which is a pressure of the air accommodated in the tank, increases. A predetermined relationship as illustrated in FIG. 8B, for example, is established between the amount of the air supplied to the tank 34 and the tank pressure. On that account, it is possible to obtain an increasing amount of the air based on an increasing amount of the tank pressure.

The switch device 36 is provided between the common passage 22, the tank 34, and the compressor device 30, and is configured to change flowing directions and the like of the air therebetween. As illustrated in FIG. 1, the common passage 22 is connected to the tank 34 via a first passage 50 and a second passage 52 provided in parallel to each other. The first passage 50 is provided with two circuit valves 61, 62 provided in series, and the second passage 52 is provided with two circuit valves 63, 64 provided in series. Further, a third passage 65 is connected between the two circuit valves 61, 62 of the first passage 50 and also connected to the intake side of the compressor 40, and a fourth passage 66 connected to the discharge side of the compressor 40 is connected between the two circuit valves 63, 64 of the second passage 52. The circuit valves 61 to 64 are normally closed valves. In an opened state, the circuit valves 61 to 64 permit bidirectional flows of the air, and in a closed state, the circuit valves 61 to 64 prevent a flow of the air from one side to the other side. However, when a pressure on the other side becomes higher than a pressure on the one side by a setting pressure or more, the circuit valves 61 to 64 permit a flow of the air from the other side to the one side. The circuit valves 61, 63 prevent an outflow of the air from the tank 34 in the closed state, the circuit valve 62 prevents an outflow of the air from the common passage 22 in the closed state, and the circuit valve 64 prevents a supply of the air to the common passage 22 in the closed state.

The exhaust valve 32 is a normally closed solenoid valve provided in the fourth passage 66 on the discharge side of the compressor 40. In an opened state of the exhaust valve 32, a discharge of the air from the fourth passage 66 to the atmospheric air (the outside of the vehicle height adjustment system) is permitted, and in a closed state thereof, the discharge of the air from the fourth passage 66 to the atmospheric air is prevented. However, when a pressure of the fourth passage 66 becomes lower than the atmospheric pressure by a setting pressure or more, a supply of the air from the atmospheric air to the fourth passage 66 is permitted. Further, a dryer 70 and a flow restraint mechanism 72 are provided in series in a part of the fourth passage 66 on a side closer to the second passage than the exhaust valve 32. The flow restraint mechanism 72 includes a differential pressure regulating valve 72$v$ and a throttling 72$s$ provided in parallel to each other. The differential pressure regulating valve 72$v$ prevents a flow of the air from a second-passage side to a compressor side, and when a pressure on the compressor side becomes higher than a pressure on the second-passage side by a setting pressure or more, the differential pressure regulating valve 72$v$ permits a flow of the air from the compressor 40 to the second passage 52.

In the present embodiment, the vehicle height adjustment system is controlled by a vehicle height adjustment ECU 80 mainly constituted by a computer. The vehicle height adjustment ECU 80 is communicable with a plurality of ECUs and the like via a CAN (Car Area Network) 82. As illustrated in FIG. 2, the vehicle height adjustment ECU 80 includes an execution portion 80$c$, a storage portion 80$m$, an input/output portion 80$i$, a timer 80$t$, and so on. A vehicle height change switch 88, a tank pressure sensor 90, a cylinder pressure sensor 91, a vehicle height sensor 93, a getting on/off-related operation detection device 95, and so on are connected to the input/output portion 80$i$, and a communications device 96, an ignition switch 98, and so on are connected thereto via the CAN 82. Further, the electric motor 42 is connected thereto via a drive circuit 100, and the exhaust valve 32, the leveling valve 26, the circuit valves 61 to 64 are connected thereto. The vehicle height change switch 88 is operated by a driver, and when an instruction to change the vehicle height to any of L (Low), N (Normal), and H (High), the vehicle height change switch 88 is operated. The tank pressure sensor 90 detects a pressure (hereinafter, just referred to as a tank pressure in some cases) of the air stored in the tank 34. The cylinder pressure sensor 91 is provided in the common passage 22, and when all the leveling valves 26 are in the closed state, the cylinder pressure sensor 91 detects a passage pressure, which is a pressure of the common passage 22. In view of this, the cylinder pressure sensor 91 can be referred to as a passage pressure sensor. The vehicle height sensor 93 is provided in each of the wheel assemblies on the front/rear and right/left sides. The vehicle height sensor 93 detects a gap from a standard length (a standard height) of a distance between the wheel-assembly-side member and the vehicle-body-side member, and outputs a vehicle height, which is the distance between the wheel-assembly-side member and the vehicle-body-side member. The getting on/off-related operation detection device 95 detects whether an operation related to getting on/off is performed or not. The getting on/off-related operation detection device 95 is provided for each of a plurality of doors provided in the vehicle, and can be configured to include a door opening/closing sensor (a courtesy lamp sensor) 102 for detecting opening/closing of a corresponding door, a door lock sensor 103 for detecting locking/unlocking of a corresponding one of the plurality of doors, and so on. Based on opening/closing of the door and whether a locking/unlocking operation of the door is performed or not, an intention of getting-on, getting-off, start, and the like is estimated. The communications device 96 communicates with a portable 104 that the driver or the like possesses, within a predetermined communicable region, and the locking/unlocking of the door may be performed by the communications therebetween. Further, the storage portion 80m stores therein a table shown in FIG. 8B, an intake control program, and the like.

In the vehicle height adjustment system configured as above, a target vehicle height is found for each of the wheel assemblies on the front/rear and right/left sides based on a running state during running of the vehicle, and the air supply/discharge device 24 and the leveling valve 26 are controlled so that an actual vehicle height of the each of the wheel assemblies approaches the target vehicle height. This makes it possible to achieve a vehicle running stability. While the vehicle stops, the vehicle height adjustment is performed when a predetermined condition is established like the following cases: a case where the vehicle height change switch 88 is operated; a case where a passenger gets on/off the vehicle; and the like cases.

Figure 3A:
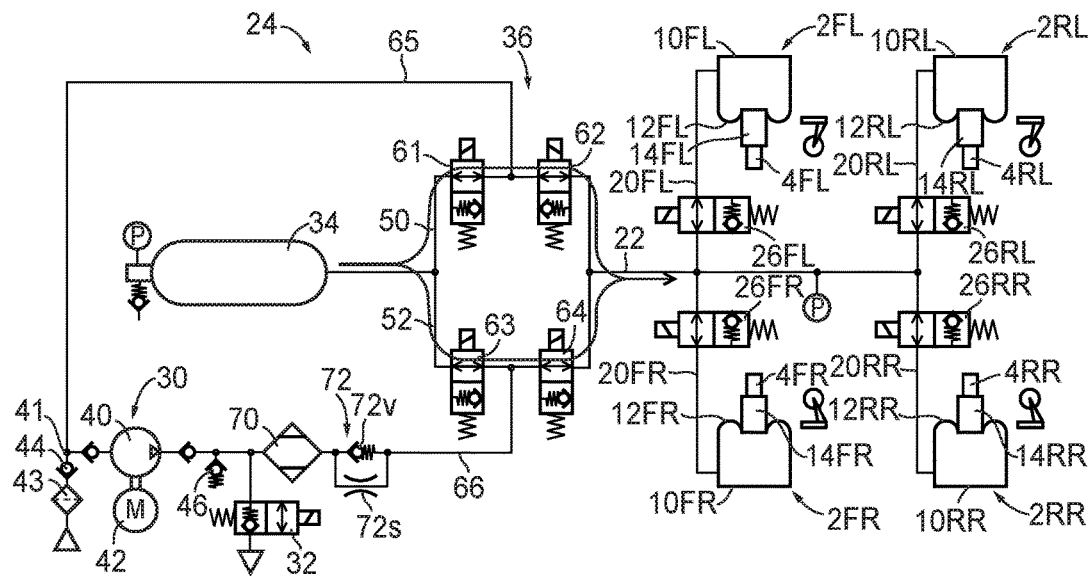
FIG. 3A is a view illustrating a state where air is supplied to an air cylinder of the vehicle height adjustment system.
Figure 3B:
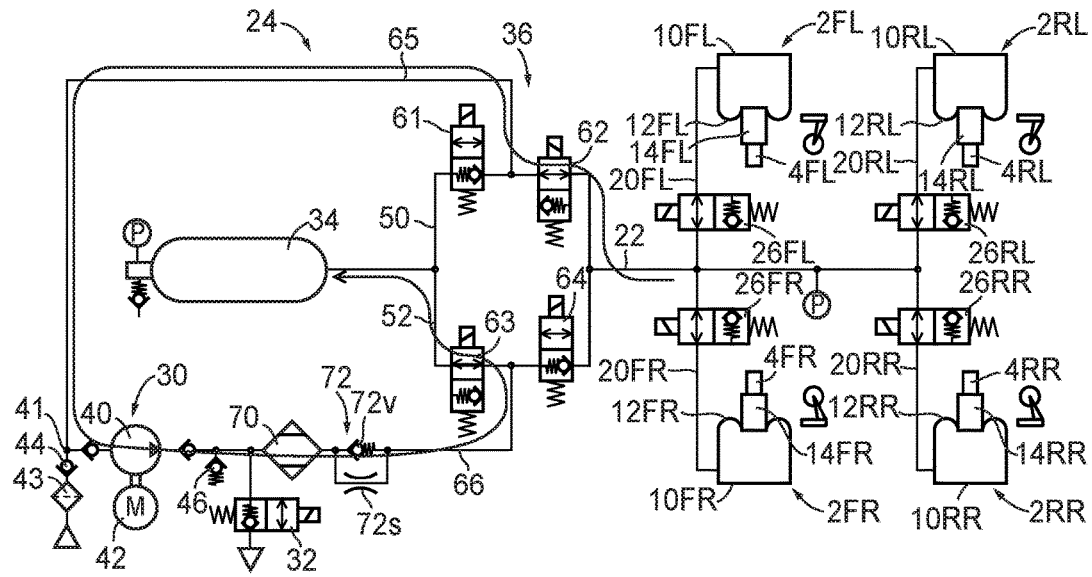
FIG. 3B is a view illustrating a state where the air is discharged from the air cylinder.

In a case where the vehicle height is increased, as illustrated in FIG. 3A, the circuit valves 61 to 64 are opened, and a leveling valve 26 corresponding to a control target wheel assembly (FIG. 3A illustrates a case where four wheel assemblies on the front/rear and right/left sides are the control target wheel assemblies) is opened. The air stored in the tank 34 is supplied to the air chamber 19 of the air cylinder 2 of the control target wheel assembly. Hereby, the vehicle height of the control target wheel assembly is increased. In a case where the vehicle height is lowered, as illustrated in FIG. 3B, the compressor 40 is operated by driving of the electric motor 42 so that the circuit valves 61, 64 are closed, the circuit valves 62, 63 are opened, and the leveling valve 26 corresponding to the control target wheel assembly is opened. The air of the air chamber 19 of the air cylinder 2 is sucked by the compressor 40 and is supplied to the tank 34.

As described above, the vehicle height adjustment is performed by use of the tank 34, but in terms of the tank pressure, an intake control to supply the air to the tank 34 and a discharge control to discharge the air from the tank 34 are performed. The present specification deals with the intake control related to the disclosure. In the intake control, the air is sucked by the operation of the compressor 40 from the outside of the vehicle height adjustment system via the intake valve 44, and then supplied to the tank 34. However, the intake valve 44 provided in the vehicle height adjustment system is a mechanical valve that is opened/closed according to a pressure difference between a high-pressure side and a low-pressure side. On that account, the intake valve 44 is not necessarily changed from the closed state to the opened state immediately after the compressor 40 is started. Further, in the closed state of the intake valve 44, the air supplied to the tank 34 by the operation of the compressor 40 is the air that has already existed inside the vehicle height adjustment system, and is not the air sucked from outside. Accordingly, an amount of the air sucked from outside via the intake valve 44 and supplied to the tank 34, that is, an intake amount cannot be acquired based on an increasing amount in the tank pressure from the starting of the compressor 40. Further, since the third passage 65 is not provided with a pressure sensor, a pressure of the air in the third passage 65 cannot be detected, so it is difficult to directly detect a change of the intake valve 44 from the closed state to the opened state. Further, if the intake valve 44 is a solenoid valve, it is possible to accurately detect a timing when the intake valve 44 is changed from the closed state to the opened state. However, a cost increases. In view of this, in the present embodiment, the intake valve 44, which is a mechanical valve, is employed so as to estimate whether or not the intake valve 44 is changed from the closed state to the opened state, based on at least one of a detection value of the tank pressure sensor 90 and a detection value of the cylinder pressure sensor 91.

Figure 4:
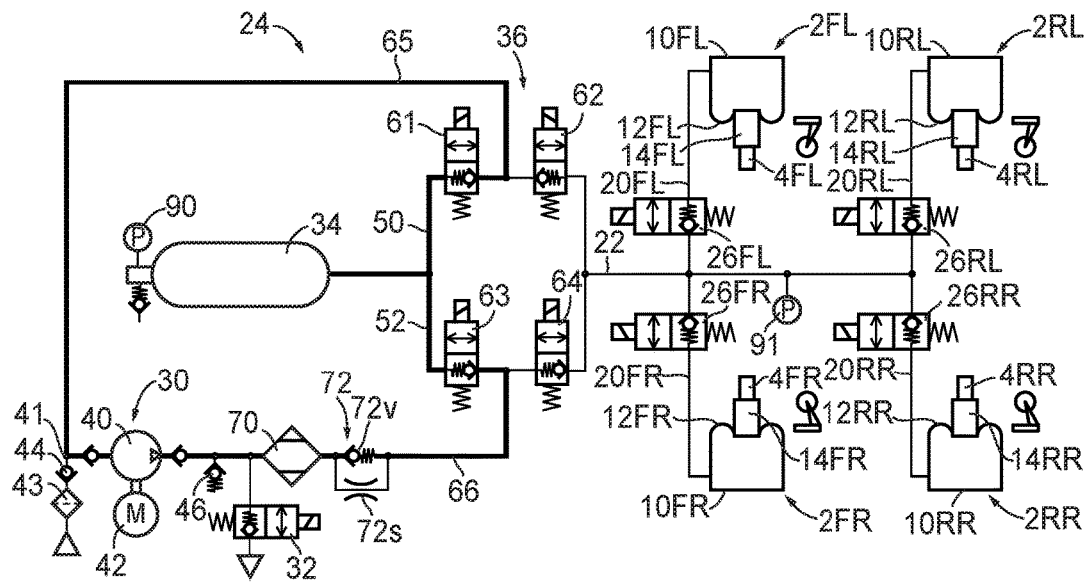
FIG. 4 is a view illustrating a normal state of the vehicle height adjustment system.
Figure 5:
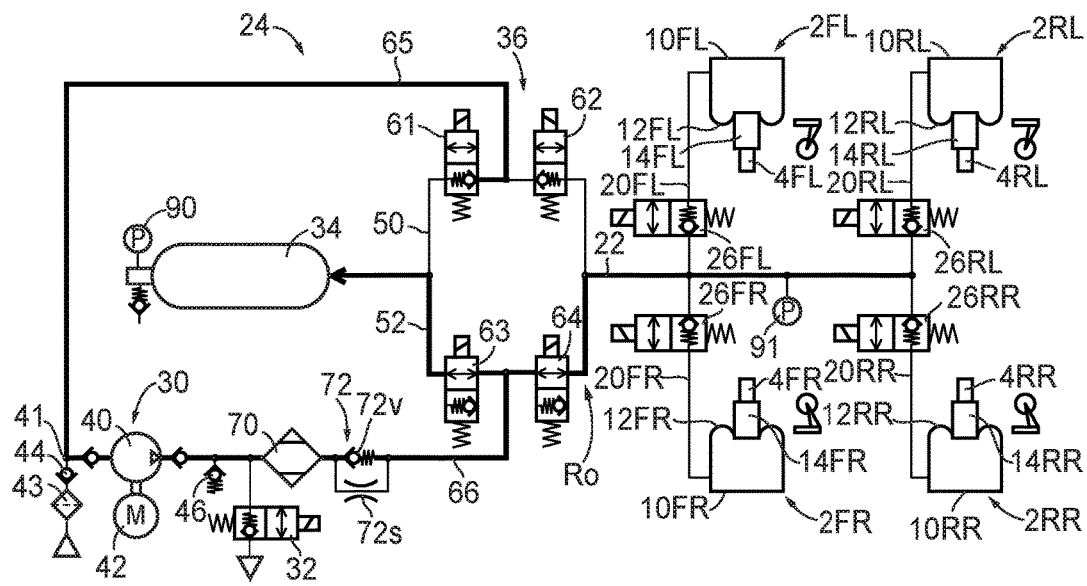
FIG. 5 is a view illustrating a state where an intake control is started in the vehicle height adjustment system.
Figure 6:
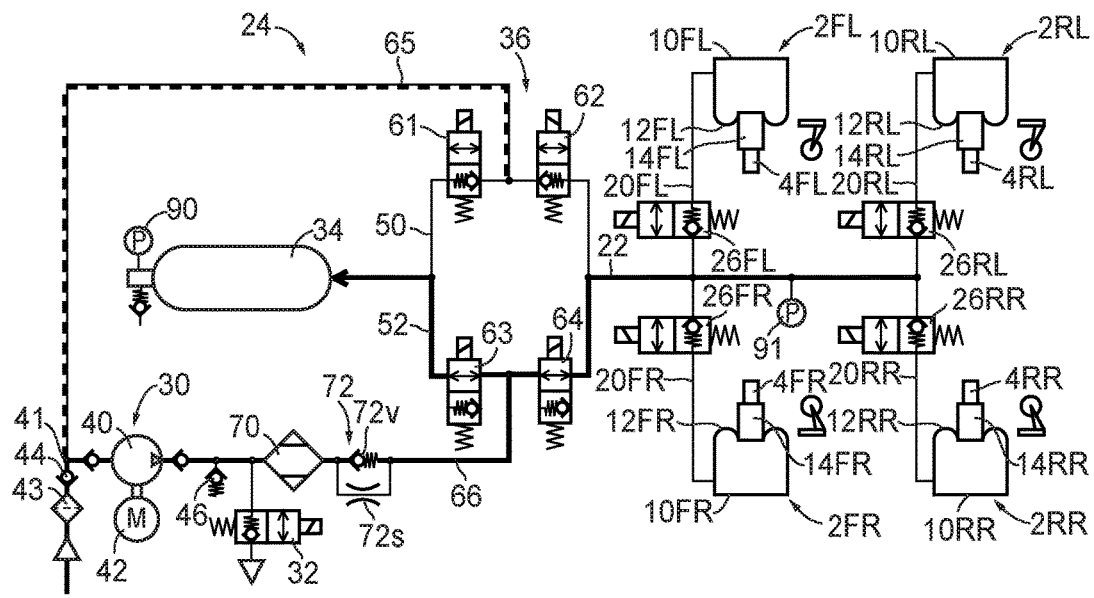
FIG. 6 is a view illustrating a state where an intake valve is changed from a closed state to an opened state in the vehicle height adjustment system.

For example, in a case where the vehicle height adjustment is finished and no current is supplied to any of the solenoid valves, the vehicle height adjustment system is in a state illustrated in FIG. 4. In this case, normally, the air exists in the third passage 65, the fourth passage 66, the first passage 50, and the second passage 52, which are indicated by a bold line, so their pressures are higher than the atmospheric pressure. When a start condition of the intake control is established, a start process is performed. As illustrated in FIGS. 5, 6, the circuit valves 61, 62 are closed and the circuit valves 63, 64 are opened, and the electric motor 42 is started so as to operate the compressor 40. Further, the leveling valve 26 is in the closed state. The third passage 65 (including the connecting portion 41) is blocked from the tank 34 and the common passage 22 (the air cylinder 2), so that an inflow of the air from both the tank 34 and the air cylinder 2 is prevented. The fourth passage 66 and the common passage 22 communicate with the tank 34 while being blocked from the air cylinder 2. Due to the operation of the compressor 40, the air of the third passage 65 is sucked and supplied to the tank 34. However, as illustrated in FIG, 5, at the beginning of the staring of the compressor 40, a pressure of the third passage 65 is higher than the atmospheric pressure, and the intake valve 44 is in the closed state. After that, due to the operation of the compressor 40, the air in the third passage 65 is sucked, so that an amount of the air therein decreases and the pressure of the third passage 65 is decreased. Then, as illustrated in FIG. 6, when the pressure of the third passage 65 (the connecting portion 41) indicated by a broken line becomes lower than the atmospheric pressure, the intake valve 44 is changed from the closed state to the opened state. Due to the compressor 40, the air is sucked from the outside (the atmospheric air) of the vehicle height adjustment system via the intake valve 44, and then supplied to the tank 34. The tank pressure increases, so that the amount of the air in the vehicle height adjustment system increases.

Figure 9:
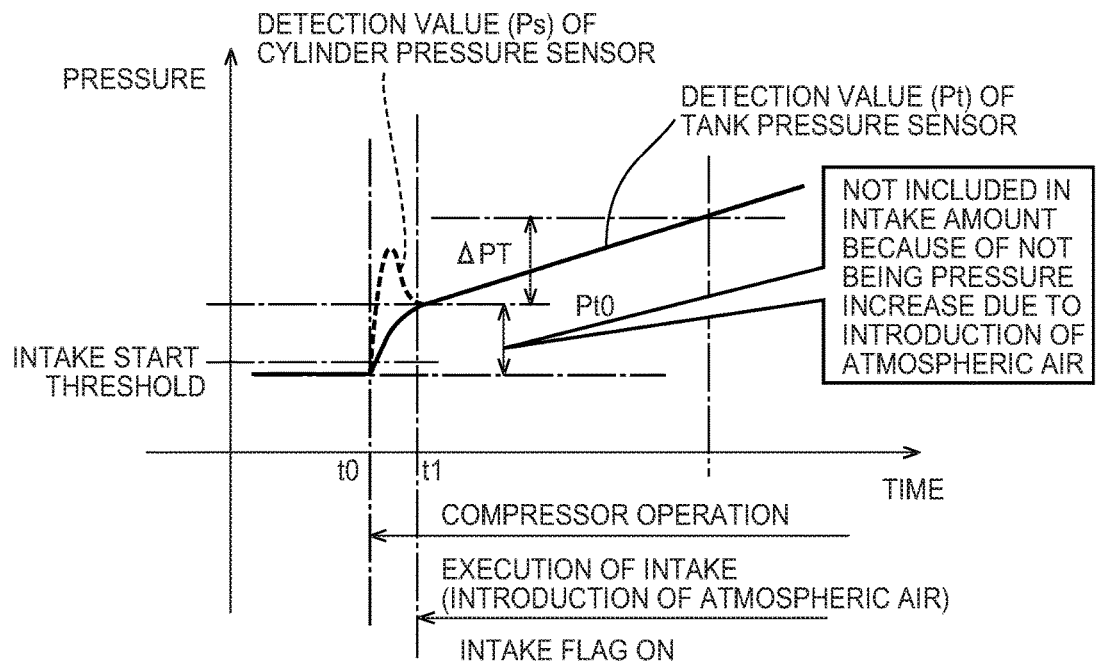
FIG. 9 is a view illustrating changes in tank pressure and passage pressure in a case where the intake control is performed in the vehicle height adjustment system.

In FIG. 9, the compressor 40 is started at a time point to. However, at the beginning of its staring, the pressure of the air in the third passage 65 is higher than the atmospheric pressure and a discharge flow rate of the air to be discharged from the compressor 40 is large. Accordingly, an increasing gradient of a tank pressure Pt, which is a detection value of the tank pressure sensor 90, is large as indicated by a continuous line. However, when the amount of the air in the third passage 65 decreases and the discharge flow rate of the air of the compressor 40 becomes small, the increasing gradient of the tank pressure Pt becomes small. Then, after the intake valve 44 is changed to the opened state at a time point t1, the discharge flow rate becomes constant and the increasing gradient of the tank pressure Pt becomes generally constant. In the meantime, since the common passage 22 and the tank 34 communicate with each other, a passage pressure Ps, which is a pressure on a discharge side, is generally the same as the tank pressure Pt regularly. However, a volume of the common passage 22 is small, so the passage pressure Ps is easily affected by the discharge flow rate of the air from the compressor 40. On that account, as indicated by a broken line in FIG. 9, the passage pressure Ps, which is a detection value of the cylinder pressure sensor 91, changes pulsingly from the time point t0 (the passage pressure Ps increases at a steep gradient and then decreases). After that, when the intake valve 44 is changed to the opened state at the time point t1 and the discharge flow rate becomes stable, the passage pressure Ps becomes generally the same as the tank pressure Pt and increases at generally the same gradient as the tank pressure Pt.

Based on the foregoing, it can be estimated that the intake valve 44 is changed from the closed state to the opened state in a case where at least one of the following conditions is established after the operation of the compressor 40 is started: (1) a condition in which the increasing gradient of the tank pressure Pt becomes small; (2) a condition in which the increasing gradient becomes constant (projects downward) after the passage pressure Ps pulsingly changes; and (3) a condition in which an absolute value of a difference between the tank pressure Pt and the passage pressure Ps tends to decrease and the absolute value of the difference becomes small. Then, based on an increasing amount $\Delta PT$ of the tank pressure PT from the time point t1 at which the intake valve 44 is estimated to be changed from the closed state to the opened state, an intake amount Q, which is an amount of the air sucked from the outside (the atmospheric air) of the vehicle height adjustment system and then supplied to the tank 34, that is, an amount of the air added into the vehicle height adjustment system can be acquired.

Figure 7:
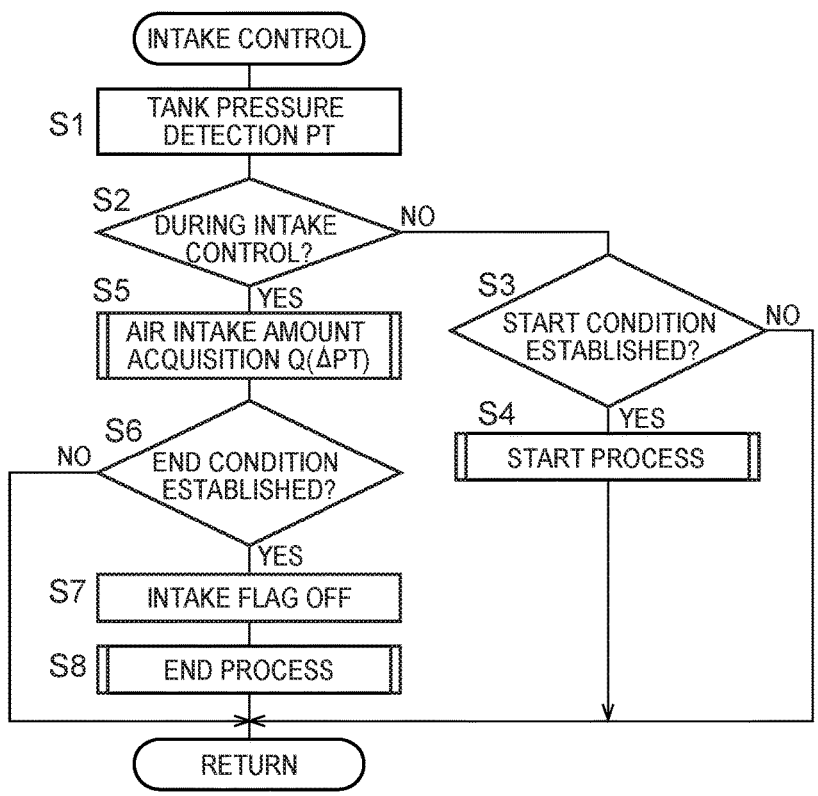
FIG. 7 is a flow chart illustrating some subroutines of an intake control program stored in a storage portion of the vehicle height adjustment ECU.

A flow chart in FIG. 7 illustrates a routine indicative of a part of the intake control program, and this routine is performed every predetermined set time. In step 1 (hereinafter referred to as S1; the other steps are expressed in the same manner), a tank pressure Pt is detected, and in S2, it is determined whether or not an intake control is being performed. When the intake control is not being performed, it is determined, in S3, whether a start condition is established or not, in other words, it is determined whether or not the air is insufficient in the tank 34. For example, in a case where the tank pressure Pt is lower than an intake start threshold, in a case where an intake amount $Q(\Delta PT)$ does not reach a target intake amount $Q^*(\Delta PTref)$, or the like case, it is determined that the start condition is established, and the start process is performed in S4. As described above, the circuit valves 63, 64 are set to the opened state, and the electric motor 42 is started, so that the compressor 40 is operated by the electric motor 42. When the intake control is started, the determination of S2 is YES. Accordingly, in S5, the intake amount $Q(\Delta PT)$ is acquired as will be described later, and in S6, it is determined whether or not an end condition is established. For example, in a case where the intake amount $Q(\Delta PT)$ reaches the target intake amount $Q^*(\Delta PTref)$, in a case where a vehicle height adjustment request is output, or the like case, it is determined that the end condition is established. When the end condition is established, an intake flag is turned off in S7 and an end process is performed in S8. For example, the compressor 40 is stopped and the circuit valves 61 to 64 are closed. As the end process, a process related to the end may be performed in some cases, or the compressor 40 may be kept operating even after the determination of S6 is YES. In a case where the end condition is established in response to the output of the vehicle height adjustment request, the intake amount $Q(\Delta PT)$ from a time point when the compressor 40 is started this time up to the present is stored. Further, the compressor 40 and the circuit valves 61 to 64 are controlled by the vehicle height adjustment control program after S8 is performed or without the execution of S8. In a case where a vehicle height adjustment request is output during the intake control, the current intake control is terminated. However, in a case where this routine is executed after the vehicle height adjustment is finished, the start condition is established due to the intake amount $Q(\Delta PT)$ not reaching the target intake amount $Q^*(\Delta PTref)$, so that the intake control is started. In the present embodiment, a control to be performed while the air is supplied to the tank 34 by one consecutive operation of the compressor 40 is referred to as the intake control.

Figure 8A:
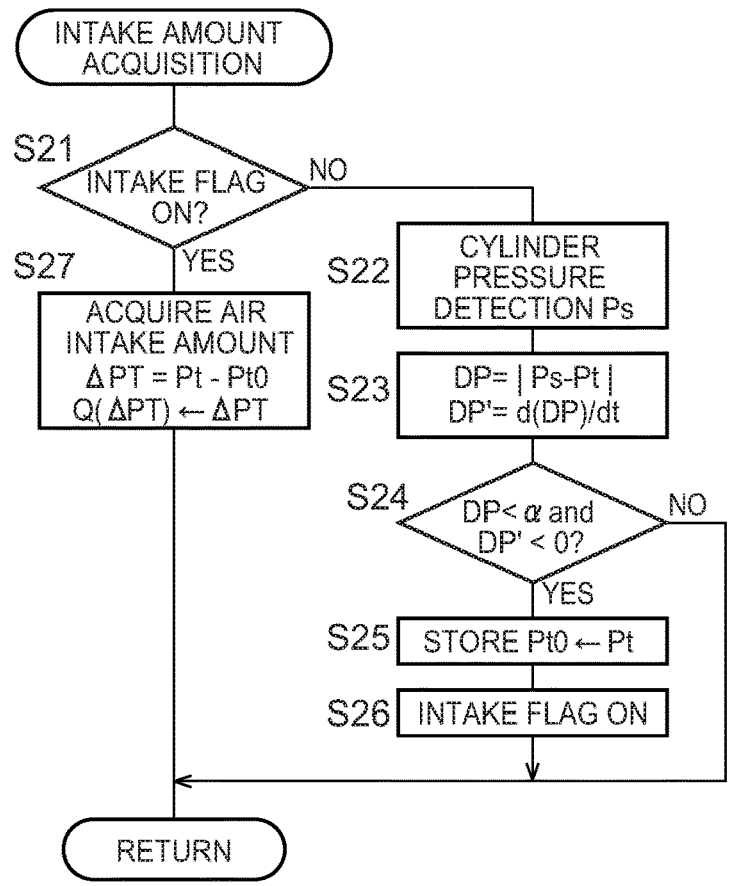
FIG. 8A is a flow chart illustrating a part of the subroutines (intake amount acquisition)
Figure 8B:
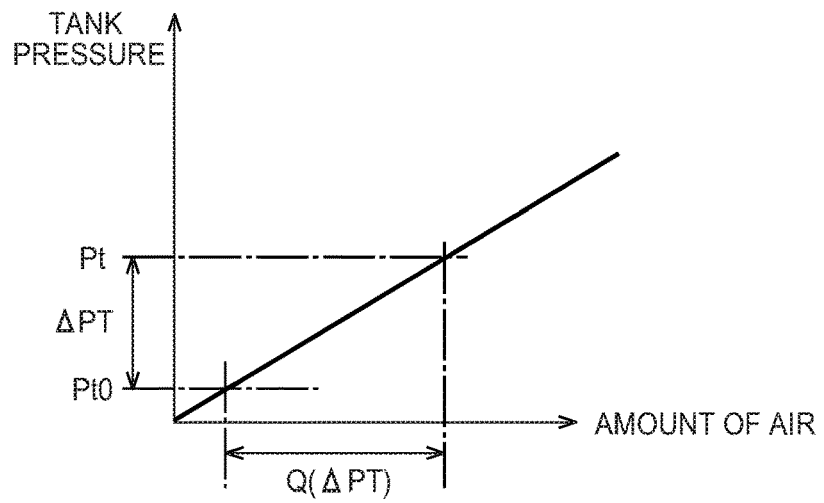
FIG. 8B is an example of a table indicative of a relationship between an increasing amount in tank pressure and an intake amount.

The acquisition of the intake amount in S5 is performed by the execution of an intake amount acquisition routine illustrated in a flow chart of FIG. 8A. In S21, it is determined whether or not the intake flag is turned on or not. The intake flag is a flag that is turned on when the intake valve 44 is opened. In a case where the intake flag is OFF, it is determined whether or not the intake valve 44 is change from the closed state to he opened state after S22. More specifically, the passage pressure Ps is detected in S22. In S23, an absolute value DP of a difference between the tank pressure Pt and the passage pressure Ps, and a change gradient DP'{=d(DP)/dt} of the absolute value of the difference with respect to a time are acquired. In S24, it is determined whether or not the absolute value DP of the difference is smaller than a set value α and whether or not the change gradient DP' is smaller than 0 (whether or not the change gradient DP' tends to decrease). In a case where the absolute value DP of the difference is the set value α or more, or in a case where the absolute value DP of the difference tends to increase, the determination is NO, so the intake flag remains OFF. In a case where the absolute value DP of the difference tends to decrease and the absolute value DP of the difference becomes smaller than the set value α while S21 to S24 are performed repeatedly, the tank pressure Pt at that time is stored as a reference pressure Pt0 and the intake flag is turned on in S25, S26. It is estimated that the intake valve 44 is changed from the closed state to the opened state.

Since the intake flag is turned on, the determination of S21 is YES. Hereby, in S27, an amount of the air sucked from the outside (the atmospheric air) of the vehicle height adjustment system and then accommodated in the tank 34, that is, the intake amount $Q(\Delta PT)$ is acquired. More specifically, by subtracting the reference pressure Pt0 stored in S25 from the tank pressure Pt detected in S1, an increasing amount $\Delta PT$ (=Pt−Pt0) of the tank pressure up to now from a time when the intake valve 44 is changed from the closed state to the opened state after the staring of the compressor 40 this time is acquired. Thus, the intake amount $Q(\Delta PT)$ is acquired based on the increasing amount $\Delta PT$ of the tank pressure and a relationship between the tank pressure and the amount of the air as illustrated in FIG. 8B.

Thus, in the present embodiment, since it is detected that the intake valve 44 is changed from the closed state to the opened state, based on the difference between the tank pressure Pt and the passage pressure Ps after the staring of the compressor 40, it is possible to accurately acquire the intake amount $Q(\Delta PT)$, which is the amount of the air sucked from the atmospheric air and supplied to the tank 34. In a case where the intake amount $Q(\Delta PT)$ reaches the target intake amount $Q^*(\Delta PTref)$ by one consecutive operation of the compressor 40, the intake control is terminated and the lack of the air is relieved. However, in a case where a vehicle height adjustment request, for example, is output during the operation of the compressor 40, or the like case, the intake control is terminated once, but the intake amount $Q(\Delta PT)$ from the starting of the compressor 40 to the stop thereof is stored. As such, in a case where the intake control is stopped due to the vehicle height adjustment or the like before the intake amount $Q(\Delta PT)$ reaches the target intake amount $Q^*(\Delta PTref)$, when a sum of respective intake amounts $Q(\Delta PT)$ for respective intake controls (performed every time when the compressor 40 is started until it is stopped) reaches the target intake amount $Q^*(\Delta PTref)$, the lack of the air is relieved. Note that, in a case where the vehicle height adjustment is performed before the intake amount $Q(\Delta PT)$ reaches the target intake amount $Q^*(\Delta PTref)$, the air is normally not discharged to the outside of the vehicle height adjustment system in the vehicle height adjustment. Accordingly, even if the tank pressure Pt changes in the vehicle height adjustment, it is possible to consider that the intake amount $Q(\Delta PT)$ accumulates.

As such, in the present embodiment, the air source device is constituted by the air supply/discharge device 24, the common passage 22, the vehicle height adjustment ECU 80, the tank pressure sensor 90, and the cylinder pressure sensor (the passage pressure sensor) 91 as the passage pressure sensor, and so on, and a suction-side portion is constituted by the third passage 65 including the connecting portion 41 or the connecting portion 41 and the like. Further, an intake control portion is constituted by the tank pressure sensor 90, the passage pressure sensor 91, and some parts of the vehicle height adjustment ECU 80. The some parts include a part for storing the intake control routine illustrated in the flow chart of FIG. 7, and a part for executing the intake control routine. Further, an intake amount acquisition portion is constituted by the tank pressure sensor 90, the passage pressure sensor 91, a part for storing the intake amount acquisition routine illustrated in the flow chart of FIG. 8, a part for executing the intake amount acquisition control routine, and the like parts. A change estimation portion is constituted by the tank pressure sensor 90, the passage pressure sensor 91, a part for storing S22 to S24, a part for executing S22 to S24, and the like parts among them. The change estimation portion is a pressure difference dependence estimation portion. Further, a compressor control portion is constituted by a part for storing S4, a part for executing S4, and the like parts.

Figure 10:
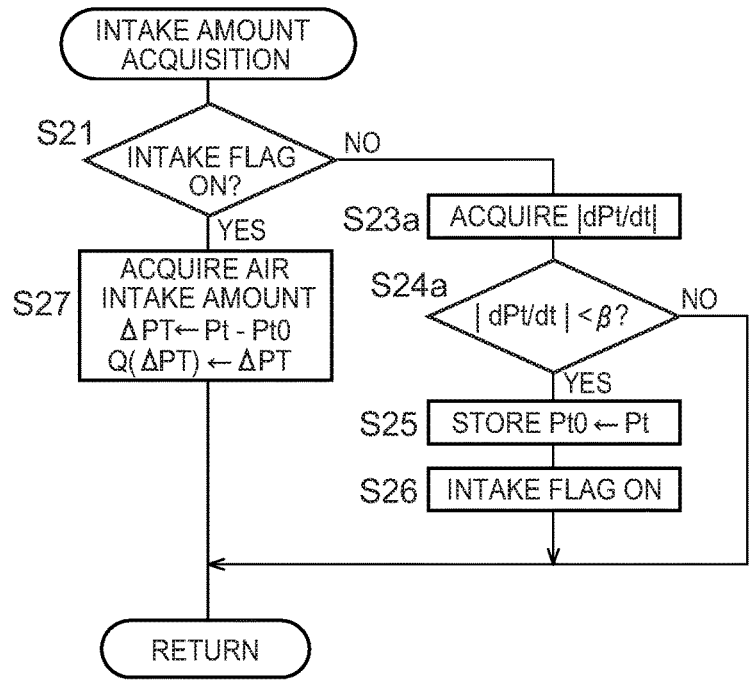
FIG. 10 is a flow chart illustrating a part (intake amount acquisition) of an intake control program stored in a storage portion of a vehicle height adjustment ECU of a vehicle height adjustment system including an air source device according to Embodiment 2 of the disclosure.

That the intake valve 44 is changed from the closed state to the opened state can be acquired based on a change in the detection value of the tank pressure sensor 90. One example thereof is described with reference to a flow chart of FIG. 10. In a case where the intake flag is OFF, an absolute value of an increasing gradient of the tank pressure is acquired in S23a, and it is determined, in S24a, whether or not the absolute value of the increasing gradient is smaller than a set value $\beta$. In a case where the absolute value of the increasing gradient becomes smaller than the set value $\beta$, it can be determined that the intake valve 44 is changed from the closed state to the opened state. The set value $\beta$ can be set to a value smaller than a gradient near a time t0, as indicated by a continuous line in FIG. 9. Since the absolute value of the increasing gradient is compared with the set value $\beta$, it is possible to successfully restrain a false determination caused due to a noise, a detection error, and the like of the tank pressure sensor 90. In the present embodiment, a tank pressure dependence estimation portion is constituted by the tank pressure sensor 90 and some parts of the vehicle height adjustment ECU 80. The some parts include a part for storing S23a, S24a of the flow chart in FIG. 10 and a part for executing S23a, S24a.

Figure 11:
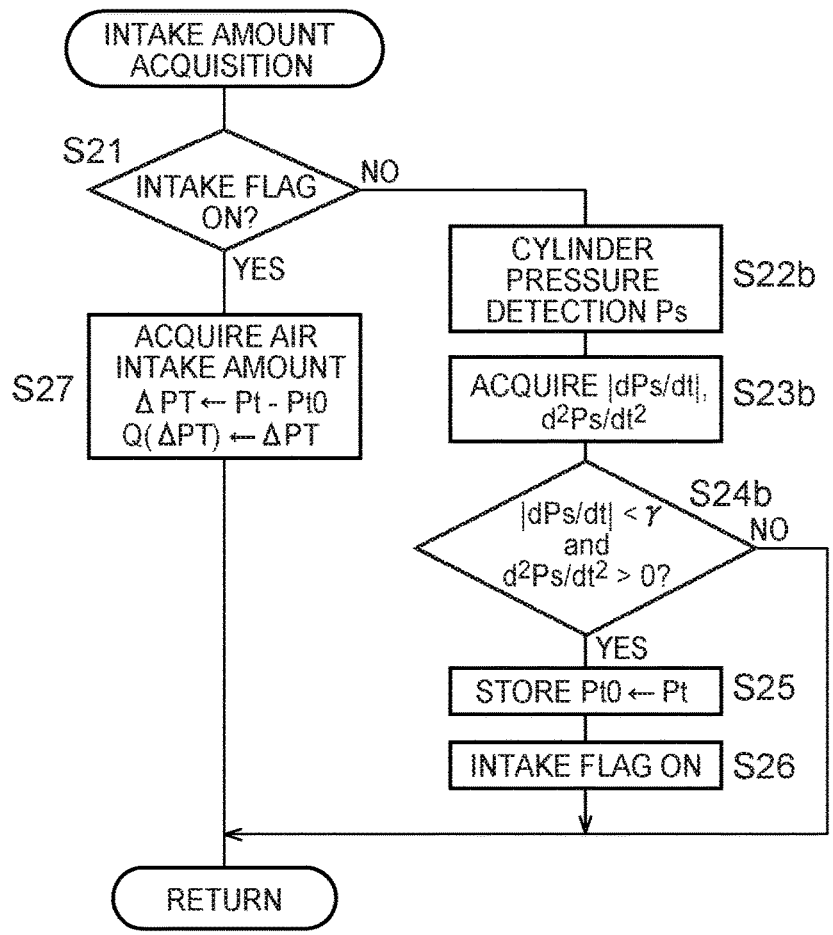
FIG. 11 is a flow chart illustrating a part (intake amount acquisition) of an intake control program stored in a storage portion of a vehicle height adjustment ECU of a vehicle height adjustment system including an air source device according to Embodiment 3 of the disclosure.

That the intake valve 44 is changed from the closed state to the opened state can be estimated based on a change in the detection value of the cylinder pressure sensor 91. One example thereof is described with reference to a flow chart of FIG. 11. In a case where the intake flag is OFF, the passage pressure Ps is acquired in S22b. In S23b, a second-order differential value of the passage pressure Ps and an absolute value of a differential value of the passage pressure Ps (an absolute value of a change gradient to time) are acquired. In S24b, it is determined whether or not the second-order differential value is a positive value and whether or not the absolute value of the differential value of the passage pressure Ps is smaller than a set value $\gamma$. In a case where a curve indicative of the passage pressure Ps projects downward and the absolute value of the differential value of the passage pressure Ps is smaller than the set value $\gamma$, it can be determined that the intake valve 44 is changed from the closed state to the opened state. In the present embodiment, a passage pressure dependence estimation portion is constituted by the passage pressure sensor 91 and some parts of the vehicle height adjustment ECU 80. The some parts include a part for storing S22b to S24b of the flow chart in FIG. 11 and a part for executing S22b to S24b.

Note that it is also possible to detect that the intake valve 44 is changed from the closed state to the opened state, based on at least two of the following states: a change state of the tank pressure; a change state of the passage pressure; and a state of a pressure difference between the tank pressure and the passage pressure. Further, it is not essential to acquire the intake amount $Q(\Delta PT)$. The increasing amount $\Delta PT$ of the tank pressure may be employed as an amount corresponding to the intake amount, and when the increasing amount $\Delta PT$ of the tank pressure reaches the target increasing amount $\Delta PTref$ corresponding to a target intake amount, it may be determined that the end condition is established. Further, the air source device is not limited to the vehicle height adjustment system, and can be applied to other in-vehicle devices (e.g., an air brake device). Further, the tank 34 has a structure and a characteristic having a relationship illustrated in FIG. 8B between the tank pressure and the amount of the air. However, the tank 34 is not limited to this. When the structure (a bladder type, a bellows type, a piston type, and the like), the characteristic (an initial pressure of an elastic body, and the like), and the like of the tank 34 change, the relationship between the increasing amount of the tank pressure and the increasing amount of the air may also change. The structure of the vehicle height adjustment system is not limited particularly. Further, the air source device according to the disclosure can be applied to an in-vehicle device operated by the air, except for the vehicle height adjustment system, and thus, the disclosure can be performed in an embodiment in which various changes and improvements are made based on the knowledge of a person skilled in the art.

An air source device according to an aspect of the disclosure includes: a tank in which air is accommodated; a compressor; an intake valve provided between a suction-side portion, which is a part on a suction side of the compressor, and an outside of the air source device, the intake valve being configured such that, when a pressure of the air in the suction-side portion is not less than an atmospheric pressure, which is a pressure of the outside, the intake valve is in a closed state, but when the pressure of the air in the suction-side portion becomes lower than the atmospheric pressure, the intake valve is changed to an opened state; and an ECU configured such that the ECU controls an amount of the air sucked from the outside and supplied to the tank by an operation of the compressor, the ECU estimates whether or not the intake valve is changed from the closed state to the opened state, based on a pressure of the air in the air source device, and the ECU acquires an intake amount, which is an amount of the air sucked from the outside and supplied to the tank by the compressor, based on an increasing amount of a tank pressure, which is a pressure of the air accommodated in the tank, the increasing amount being an increasing amount from a time point when the intake valve is estimated to be changed from the closed state to the opened state. It is normal that the air exists in the air source device. Accordingly, in a case where the compressor is operated in the closed state of the intake valve, the air in the air source device is circulated and accommodated in the tank, so that the amount of the air in the air source device does not increase. On the other hand, in a case where the compressor is operated in the opened state of the intake valve, it is considered that the air is sucked from the outside and is supplied to the tank. However, the intake valve is a mechanical valve configured to be changed from the closed state to the opened state when the pressure of the air in the suction-side portion of the compressor becomes lower than the atmospheric pressure, and it is difficult to directly detect opening/closing of the intake valve. In view of this, in the air source device according to the aspect, it is detected that the intake valve is changed from the closed state to the opened state, based on the pressure of the air in the air source device, a pressure change, and the like, and the intake amount is acquired based on an increasing amount of the tank pressure from a time point when the intake valve is changed from the closed state to the opened state. As a result, it is possible to accurately acquire the intake amount, which is the amount of the air sucked from the outside and supplied to the tank. In the above aspect, the air source device may further include a tank pressure sensor configured to detect the tank pressure as the pressure of the air in the air source device, the tank pressure being a pressure of the air accommodated in the tank. Further, the ECU may estimate whether or not the intake valve is changed from the closed state to the opened state, based on an increasing state of the tank pressure. The compressor is operated in a state where the air is prevented from flowing into the suction-side portion (including the connecting portion of the intake valve) from both the tank and the actuator, the suction-side portion being a part on the intake side of the compressor. The air of the suction-side portion is circulated and supplied to the tank (i), but after that, an amount of the air in the suction-side portion decreases (ii), and when the pressure of the air becomes lower than the atmospheric pressure, the intake valve is opened, so that the air is sucked into the air source device from its outside and supplied to the tank. In a state of (i), the air is supplied to the tank at a large flow rate, so the tank pressure increases at a large gradient. However, in a state of (ii), the flow rate of the air supplied to the tank becomes small, so the increasing gradient of the tank pressure becomes small. After that, the air is sucked from the outside, so the increasing gradient becomes generally constant. Based on the above-mentioned circumstances, in a case where the increasing gradient of the tank pressure relative to time becomes small from a large state, in a case where the increasing gradient decreases by a set value or more, or the like case, it can be determined that the pressure of the air in the suction-side portion of the compressor becomes lower than the atmospheric pressure and the intake valve is changed from the closed state to the opened state. In the above aspect, the air source device may further include a passage pressure sensor configured to detect, as the pressure of the air in the air source device, a pressure of the air in a discharge passage connected to a discharge side of the compressor. Further, the ECU may estimate whether or not the intake valve is changed from the closed state to the opened state, based on a change state of the pressure of the air in the discharge passage. The discharge passage of the compressor is blocked from the actuator and communicates with the tank. In a state where the discharge passage communicates with the tank, the tank pressure is generally the same as the pressure of the air in the discharge passage, regularly. However, a volume of the discharge passage is smaller than the tank, so the pressure of the air in the discharge passage is easily affected by a flow rate of the air discharged from the compressor. In the state of (i), the pressure of the air in the discharge passage increases transiently. However, in the state of (ii), the pressure of the air in the discharge passage becomes generally the same as the tank pressure, and then increases in a similar manner to the tank pressure. Based on the above-mentioned circumstances, at a time point when the pressure of the air in the discharge passage decreases after the pressure increases, and then starts to increase, for example, in a case where a second-order differential value of the pressure of the air in the discharge passage is a positive value and an absolute value of a differential value thereof is smaller than a set value, it can be estimated that the intake valve is changed from the closed state to the opened state. In the above aspect, the air source device may further include: the tank pressure sensor configured to detect the tank pressure as the pressure of the air in the air source device, the tank pressure being a pressure of the air accommodated in the tank; and the passage pressure sensor configured to detect, as the pressure of the air in the air source device, the pressure of the air in the discharge passage connected to the discharge side of the compressor. The ECU may estimate whether or not the intake valve is changed from the closed state to the opened state, based on a difference between the tank pressure and the pressure of the air in the discharge passage. As described above, the detection value of the passage pressure sensor decreases after it transiently increases, and then the detection value becomes generally the same as the detection value of the tank pressure sensor. In other words, after an absolute value of a difference between the detection values of two sensors becomes large, the absolute value comes closer to 0. Accordingly, when the absolute value of the difference therebetween decreases and comes closer to 0, it can be estimated that the intake valve is changed from the closed state to the opened state. In the above aspect, when a set time has passed from a start of an operation of the compressor, the ECU may detect that the intake valve is changed from the closed state to the opened state. Based on the volume of the suction-side portion, an operating condition of the compressor, and the like, it is possible to roughly find a time from an operation start of the compressor until the pressure of the air in the suction-side portion becomes lower than the atmospheric pressure and the intake valve is changed from the closed state to the opened state. Accordingly, when the set time has passed from the operation start, it can be detected that the intake valve is changed from the closed state to the opened state. Note that the set time can be acquired more accurately when the pressure of the air in the suction-side portion just before the staring of the compressor is found. However, it is not essential to acquire the pressure of the air in the suction-side portion just before the starting. In the above aspect, an actuator operated by the air may be connected to the air source device, and the ECU may control the compressor to be operated in a state where inflows of the air to the suction-side portion from the tank and the actuator are both prevented. Further, in the above configuration, the ECU may control the compressor to be operated in a state where the discharge passage connected to the discharge side of the compressor communicates with the tank, and the discharge passage is blocked from the actuator. Further, in the above aspect, when a start condition is established, the ECU may control the compressor to start, and when an end condition is established, the ECU may control the compressor to stop. Further, in the above aspect, the actuator may be an air cylinder provided for a wheel assembly of a vehicle and provided between a wheel-assembly-side member and a vehicle-body-side member.

What is claimed is:

1. An air source device comprising:
a tank in which air is accommodated;
a compressor;
an intake valve provided between a suction-side portion, which is a part on a suction side of the compressor, and an outside of the air source device, the intake valve being configured such that, when a pressure of the air in the suction-side portion is not less than an atmospheric pressure, which is a pressure of the outside, the intake valve is in a closed state, but when the pressure of the air in the suction-side portion becomes lower than the atmospheric pressure, the intake valve is changed to an opened state; and
an ECU configured such that the ECU controls an amount of the air sucked from the outside and supplied to the tank by an operation of the compressor, the ECU estimates whether or not the intake valve is changed from the closed state to the opened state, based on a pressure of the air in the air source device, and the ECU acquires an intake amount, which is an amount of the air sucked from the outside and supplied to the tank by the compressor, based on an increasing amount of a tank pressure, which is a pressure of the air accommodated in the tank, the increasing amount being an increasing amount from a time point when the intake valve is estimated to be changed from the closed state to the opened state.

2. The air source device according to claim 1, further comprising
a tank pressure sensor configured to detect the tank pressure as the pressure of the air in the air source device, the tank pressure being a pressure of the air accommodated in the tank, wherein
the ECU estimates whether or not the intake valve is changed from the closed state to the opened state, based on an increasing state of the tank pressure.

3. The air source device according to claim 1, further comprising
a passage pressure sensor configured to detect, as the pressure of the air in the air source device, a pressure of the air in a discharge passage connected to a discharge side of the compressor, wherein
the ECU estimates whether or not the intake valve is changed from the closed state to the opened state, based on a change state of the pressure of the air in the discharge passage.

4. The air source device according to claim 1, further comprising:
a tank pressure sensor configured to detect the tank pressure as the pressure of the air in the air source device, the tank pressure being a pressure of the air accommodated in the tank; and
a passage pressure sensor configured to detect, as the pressure of the air in the air source device, the pressure of the air in the discharge passage connected to a discharge side of the compressor, wherein
the ECU estimates whether or not the intake valve is changed from the closed state to the opened state, based on a difference between the tank pressure and the pressure of the air in the discharge passage.

5. The air source device according to claim 1, wherein:
an actuator operated by the air is connected to the air source device; and
the ECU controls the compressor to be operated in a state where inflows of the air to the suction-side portion from the tank and the actuator are both prevented.

6. The air source device according to claim 5, wherein the ECU controls the compressor to be operated in a state where a discharge passage connected to the discharge side of the compressor communicates with the tank, and the discharge passage is blocked from the actuator.

* * * * *